United States Patent [19]

Kleiner

[11] Patent Number: 5,155,257
[45] Date of Patent: Oct. 13, 1992

[54] PROCESS FOR THE PREPARATION OF ACYLAMINOMETHANEPHOSPHONIC ACIDS

[75] Inventor: Hans-Jerg Kleiner, Kronberg/Taunus, Fed. Rep. of Germany

[73] Assignee: Hoechst Aktiengesellschaft, Frankfurt am Main, Fed. Rep. of Germany

[21] Appl. No.: 774,511

[22] Filed: Oct. 8, 1991

[30] Foreign Application Priority Data

Oct. 10, 1990 [DE] Fed. Rep. of Germany ....... 4032102

[51] Int. Cl.⁵ .............................................. C07F 9/38
[52] U.S. Cl. ......................................... 562/15; 562/16
[58] Field of Search ..................... 562/15, 16

[56] References Cited

U.S. PATENT DOCUMENTS 2,304,156 12/1942 Engelmann et al. ............... 554/40
2,328,358 8/1943 Pikl ..................................... 562/16
4,851,159 7/1989 Fields et al. ...................... 562/17

Primary Examiner—Jose G. Dees
Assistant Examiner—B. Frazier
Attorney, Agent, or Firm—Curtis, Morris & Safford

[57] ABSTRACT

Acylaminomethanephosphonic acids are useful intermediates for the preparation of the herbicide N-phosphonemethylglycine and its salts.

According to the invention, acylaminomethanephosphonic acids of the formula (I)

$$R^1-CO-NHCH_2P(=O)(OH)_2 \qquad (I)$$

in which $R^1$ is H, $C_1-C_6$-alkyl, benzyl or optionally substituted phenyl, can be prepared in a process which can be employed industrially, which comprises the reaction of the compound of the formula $R^1-CO-NH-CH_2OH$ with $P_2O_3$ and then hydrolysis with water.

17 Claims, No Drawings

PROCESS FOR THE PREPARATION OF ACYLAMINOMETHANEPHOSPHONIC ACIDS

DESCRIPTION

Acylaminomethanephosphonic acids are useful intermediates for the preparation of aminomethanephosphonic acid, which is of industrial interest. In particular, they are also suitable as intermediates for the preparation of herbicidally active N-phosphonomethylglycine by reaction with glyoxylic acid (see U.S. Pat. No. 4,851,159). Until now, the acylaminomethanephosphonic acids were obtainable, for example, by reaction of N-hydroxymethylamides with phosphorus trichloride and subsequent hydrolysis with the formation of hydrochloric acid (U.S. Pat. No. 2,304,156; U.S. Pat. No. 2,328,358). A particular disadvantage of this process consists in the formation of bischloromethyl ether as an undesired by-product, which has been identified as a carcinogenic working material. Bischloromethyl ether is formed by reaction of formaldehyde and hydrochloric acid in the hydrolysis step, the formaldehyde being present in traces in the N-hydroxymethylamides as a result of the preparation. The residue-free removal of bischloromethyl ether requires complicated purification steps. The object is thus to make available a process which excludes the formation of bischloromethyl ether and can be used industrially.

The invention relates to a process for the preparation of compounds of the formula I

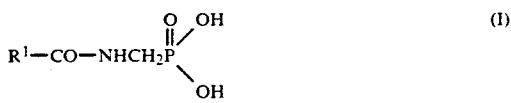  (I)

in which $R^1$ is H, $C_1$-$C_6$-alkyl, preferably $C_1$-$C_3$-alkyl, benzyl or phenyl, which is unsubstituted or substituted by one or more radicals from the group comprising $C_1$-$C_4$-alkyl, $C_1$-$C_4$-alkoxy and halogen, which comprises reacting compounds of the formula II

  (II)

in which $R^1$ has the abovementioned meaning, with diphosphorus trioxide ($P_2O_3$) and then hydrolyzing with water.

Examples of suitable starting compounds of the formula II for the process according to the invention are: N-hydroxymethylformamide, N-hydroxymethylacetamide and in particular N-hydroxymethylbenzamide.

The compounds of the formula II can be employed in pure form or prepared in situ, for example as the crude product prepared from the corresponding amides and paraformaldehyde, if appropriate in a solvent such as acetic acid.

Of particular importance to the size of the yield is the molar ratio of the components to one another. The starting substances N-hydroxymethylamide of the formula II and $P_2O_3$ are preferably employed in a molar ratio of at most 2:1, in particular in a molar ratio of 2:1 to 1.5:1. The molar ratio 2:1 is as a rule preferred, but a slight excess of $P_2O_3$ can be advantageous.

After reaction is complete, the mixture is hydrolyzed with water, a molar ratio of water to $P_2O_3$ employed of at least 1:1 being advantageous. An excess of water is possible, preferably up to a molar ratio of water to $P_2O_3$ of 5:1. If no hydrolysis with water is carried out, then the final products of the reaction are pyrophosphonic acids of the formula III

  (III)

The reaction of compounds of the formula II and $P_2O_3$ is preferably carried out in an organic solvent.

Suitable organic solvents are particularly polar protic or polar aprotic organic solvents which are inert under the reaction conditions, such as acetic acid, acetonitrile, tetrahydrofuran and dioxane. Preferred solvents are tetrahydrofuran and acetic acid.

The process is advantageously carried out, for example, in such a way that the reaction component of the formula II and $P_2O_3$ are mixed in a temperature range from 5° to 60° C., if appropriate with cooling. The sequence of the addition of the components is not critical in this case. For example, the N-hydroxymethylamide of the formula II, if appropriate dissolved in an organic solvent, can be metered into the solution of $P_2O_3$ in an organic solvent. The reaction mixture obtained is optionally additionally stirred, for example in a temperature range from 10 to 60° C., and then heated to a temperature of 60° to 200° C., in particular 65° to 150° C. It is preferably heated to reflux in this case, but it may be appropriate to work under pressure to increase the reaction temperature. After reaction is complete, the mixture is allowed to cool and is treated with water or with a water-containing mixture, for example a water-containing organic solvent. To accelerate the commencing hydrolysis, an increase in temperature, for example up to reflux temperature, may be appropriate. The temperature during the hydrolysis is preferably from 10° to 200° C., in particular 60° to 120° C. After the hydrolysis and cooling of the reaction mixture, the product can be worked up and further purified by customary methods. For work-up, for example, the organic solvent optionally added in the previous reactions is first removed, for example by distillation, if appropriate under reduced pressure. However, the reaction material, for example, can also be separated in crystallized form from the organic solvent by filtering with suction. The crude products can be further purified in a simple manner by crystallization.

The process according to the invention permits the preparation of acylaminomethanephosphonic acids in high yield under conditions which can be employed industrially. The formation of undesired bischloromethyl ether is avoided.

EXAMPLE 1

11 g (0.1 mol) of diphosphorus trioxide ($P_2O_3$) were dissolved in 70 ml of tetrahydrofuran and the solution was cooled to 5° C. 30.2 g (0.2 mol) of N-hydroxymethylbenzamide were then added in portions at 5°-10° C. in the course of 30 minutes with stirring and under a nitrogen atmosphere. The mixture was then allowed to come to room temperature with stirring and was then heated to reflux for 2 hours; a clear solution was not formed in this case. After cooling to room temperature, 4.5 g (0.25 mol) of water were added dropwise at 30°-40° C. and the mixture was then heated to reflux for 1 hour. It was then cooled, additionally stirred and filtered with suction. 28.5 g of benzoylaminomethanephosphonic acid having a melting point of 171° to 173° C. were obtained. A further 5 g were isolated from the mother liquor. Altogether, 33.5 g (78% of theory) of product were thus obtained.

EXAMPLE 2

30.2 g (0.2 mol) of N-hydroxymethylbenzamide were dissolved in 50 ml of tetrahydrofuran and cooled to 5° C. with stirring, then a solution of 11 g (0.1 mol) of diphosphorus trioxide ($P_2O_3$) in 20 ml of tetrahydrofuran was added dropwise at 5°–15° C. during the course of 30 minutes under a nitrogen atmosphere. The reaction solution obtained was then cooled to 2° C. for 10 minutes. Cooling was then omitted, the internal temperature rising to 35° C. The mixture was then heated to reflux for 2 hours; a clear solution was not formed in this case. It was then cooled. 4.5 g (0.25 mol) of water were then added dropwise at 30°–35° C. with cooling. The mixture was then heated to reflux for 1 hour, then cooled and additionally stirred and finally filtered with suction. 25 g of benzoylaminomethanephosphonic acid having a melting point of 175° to 178° C. were obtained. A further 5.5 g were isolated from the mother liquor. Altogether, 30.5 g (71% of theory) of product were thus obtained.

EXAMPLE 3

50 ml of acetic acid were cooled to 10° C. with stirring and under a nitrogen atmosphere. 11 g (0.1 mol) of diphosphorus trioxide ($P_2O_3$) were then added dropwise with further cooling, during the course of which the temperature fell to 0° to 5° C. 30.2 g (0.2 mol) of N-hydroxymethylbenzamide were then added in portions at 5°–10° C. during the course of 60 minutes. The mixture was then stirred without cooling until room temperature was reached. It was then heated to reflux for 3½ hours. It was then cooled. 2 g (0.11 mol) of water were then added dropwise with stirring, the temperature rising to 35° C. The mixture was then allowed to cool and 25 ml of acetone were added. It was then additionally stirred and filtered with suction. 31.5 g of benzoylaminomethanephosphonic acid having a melting point of 165° to 170° C. were obtained. A further 2 g were isolated from the mother liquor. Altogether, 33.5 g (78% of theory) were thus obtained.

EXAMPLE 4

20 g (0.225 mol) of N-hydroxymethylacetamide were dissolved in 20 ml of acetic acid and cooled to 5° C. under a nitrogen atmosphere and with stirring. 12.4 g (0.113 mol) of diphosphorus trioxide ($P_2O_3$) were then added dropwise at 5° to 10° C. with stirring during the course of 20 minutes. The mixture was then stirred without cooling until room temperature was reached. It was then heated to reflux for 3½ hours. It was then cooled. 2 g (0.11 mol) of water were then added dropwise with stirring, the temperature rising to 35° C. After cooling, the acetic acid was removed under reduced pressure and with continuous warming to 95° C. The crystalline residue was digested with ethanol. 26 g of crude acetylaminomethanephosphonic acid having a melting point of 171°–175° C. were obtained. After recrystallization from 88% strength aqueous acetic acid, 19 g (55% of theory) of acetylaminomethanephosphonic acid having a melting point of 186° to 90° C. were obtained. The CHNP elemental analysis of a sample gave:

$C_3H_8NO_4P$ calc.: 23.53% C 5.23% H 9.15% N 20.26% P; (153) found: 22.6% C 5.1% H 8.7% N 20.4% P.

I claim:

1. A process for the preparation of a compound of the formula I

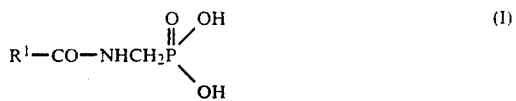

in which $R^1$ is H, $C_1$–$C_6$-alkyl, benzyl or phenyl, which is unsubstituted or substituted by one or more radicals from the group comprising $C_1$–$C_4$-alkyl, $C_1$–$C_4$-alkoxy and halogen, which comprises reacting a compound of the formula II

in which $R^1$ has the abovementioned meaning, with diphosphorus trioxide ($P_2O_3$) and then hydrolyzing with water.

2. The process as claimed in claim 1, wherein $R^1$ is H, $C_1$–$C_3$-alkyl, benzyl or phenyl.

3. The process as claimed in claim 1, wherein $R^1$ is hydrogen, methyl, ethyl or phenyl.

4. The process as claimed in claim 1, wherein $R^1$ is methyl.

5. The process as claimed in claim 1, wherein $R^1$ is phenyl.

6. The process as claimed in claim 1, wherein the compound of the formula II and $P_2O_3$ are reacted in a molar ratio II:$P_2O_3$ of at most 2:1.

7. The process as claimed in claim 6, wherein the molar ratio is from 2:1 to 1.5:1.

8. The process as claimed in claim 1, wherein the reaction temperature for the reaction with $P_2O_3$ is 60° to 200° C.

9. The process as claimed in claim 1, wherein the hydrolysis is carried out with water in a molar ratio of water to $P_2O_3$ employed of at least 1:1 and at a temperature of 10° to 200° C.

10. The process as claimed in claim 1, wherein the reaction of the compound of the formula II and $P_2O_3$ is carried out in the presence of an organic solvent.

11. The process as claimed in claim 10, wherein the solvent is an inert polar protic or aprotic organic solvent.

12. The process as claimed in claim 6, wherein $R^1$ is H, $C_1$–$C_3$-alkyl, benzyl or phenyl.

13. The process as claimed in claim 12, wherein the molar ratio is from 2:1 to 1.5:1.

14. The process as claimed in claim 12, wherein the reaction temperature for the reaction with $P_2O_3$ is 60° to 200° C.

15. The process as claimed in claim 13, wherein the reaction temperature for the reaction with $P_2O_3$ is 60° to 200° C.

16. The process as claimed in claim 12, wherein the hydrolysis is carried out with water in a molar ratio of water to $P_2O_3$ employed of at least 1:1 and at a temperature of 10° to 200° C.

17. The process as claimed in claim 16, wherein the reaction temperature for the reaction with $P_2O_3$ is 60° to 200° C.

* * * * *